US00PP21956P2

(12) United States Plant Patent
Roberson

(10) Patent No.: US PP21,956 P2
(45) Date of Patent: May 31, 2011

(54) ***CANNA* PLANT NAMED 'CAN DO PINK'**

(50) Latin Name: *Canna generalis*
Varietal Denomination: Can Do Pink

(76) Inventor: Robert Roberson, Grain Valley, MO (US)

( * ) Notice: Subject to any disclaimer, the term of this patent is extended or adjusted under 35 U.S.C. 154(b) by 0 days.

(21) Appl. No.: 12/657,103

(22) Filed: Jan. 13, 2010

(51) Int. Cl.
*A01H 5/00* (2006.01)

(52) U.S. Cl. ..... Plt./415

(58) Field of Classification Search ..... Plt./415
See application file for complete search history.

*Primary Examiner* — Annette H Para

(57) ABSTRACT

A new and distinct *Canna* cultivar named 'Can Do Pink' is disclosed, characterized by short, compact growth habit. Flowers are characteristically large, pink and rapidly self-cleaning. The new cultivar is a *Canna,* typically suited for garden and ornamental container use.

1 Drawing Sheet

Figure 1:
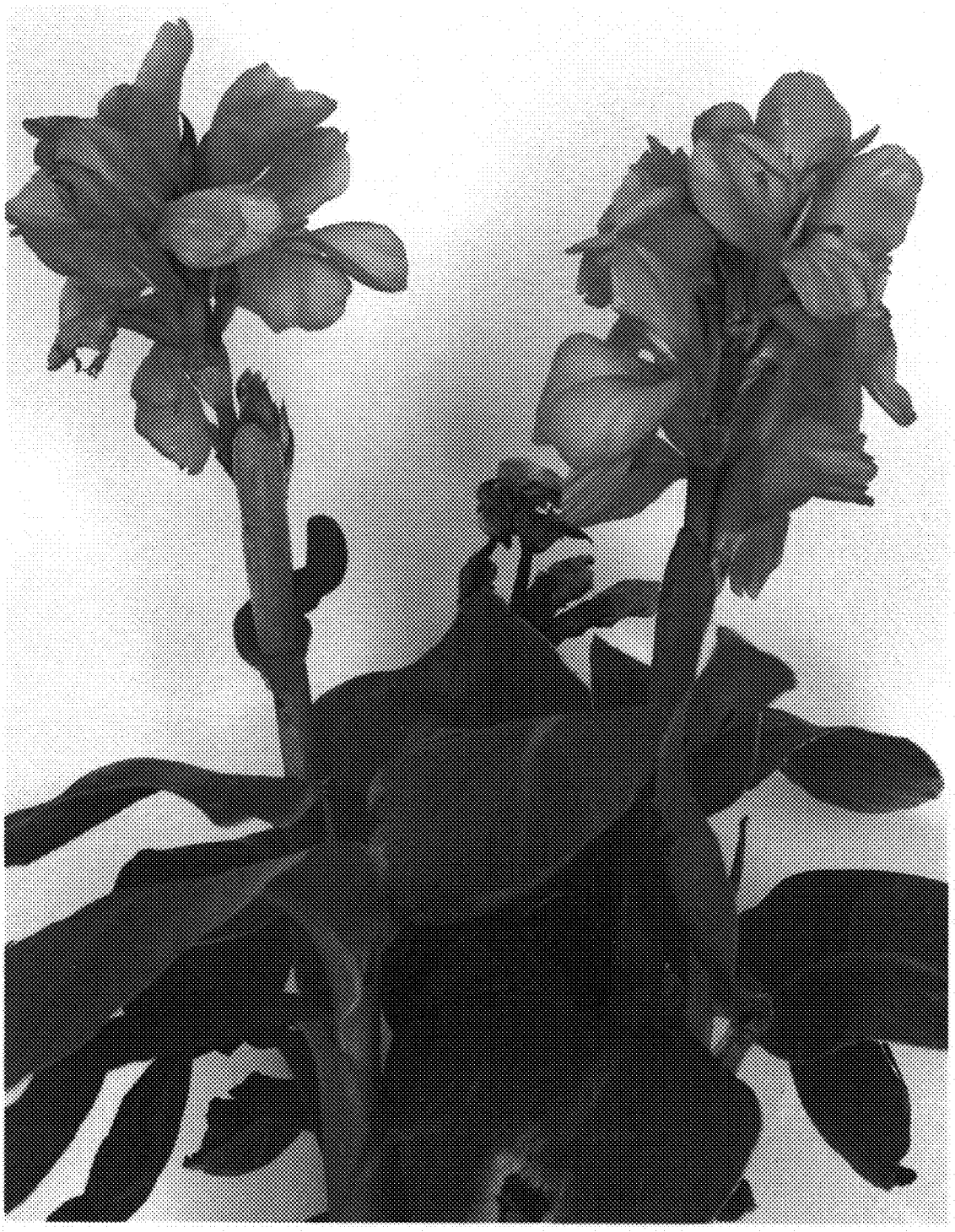

Latin name of the genus and species: *Canna generalis.*
Variety denomination: 'Can Do Pink'.

BACKGROUND OF THE INVENTION

The new cultivar is a product of a planned breeding program. The new variety originated from a cross pollination of the seed parent, an unpatented variety of *Canna generalis* known as 'Liberty Pink' with the pollen parent, an unpatented proprietary selection of *Canna generalis* referred to as 'Roberson Seedling' directed by the inventor in August of 2003. The crossing was made in Grain Valley, Mo., at a commercial greenhouse.

'Can Do Pink' was discovered by the inventor, James Roberson, in July 2004 in Grain Valley, Mo., at a commercial greenhouse among seedlings resulting from the 2003 crossing.

Asexual reproduction of the new cultivar 'Can Do Pink' was first performed in Grain Valley Mo., at a commercial greenhouse by vegetative divisions in October 2004. 'Can Do Pink' has since produced at least five generations and has shown that the unique features of this cultivar are stable and reproduced true to type.

SUMMARY OF THE INVENTION

The cultivar 'Can Do Pink' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Can Do Pink.' These characteristics in combination distinguish 'Can Do Pink' as a new and distinct *Canna* cultivar:

1. Exceptionally short overall plant height, approximately 24 inches when mature.
2. Characteristic low seed set.
3. Large pink bloom head.
4. Rapid self cleaning flowering habit.

PARENTAL COMPARISON

Plants of the new cultivar 'Can Do Pink' are similar to the female parent 'Liberty Pink' in most horticultural characteristics. However, 'Can Do Pink' differs in producing shorter, more compact plants than 'Liberty Pink' Additionally, 'Can Do Pink' produces a more true pink flower, whereas 'Liberty Pink' produces a more Salmon Pink flower. 'Can Do Pink' also has significantly lighter colored foliage than 'Liberty Pink.'

Plants of the new cultivar 'Can Do Pink' are similar to the male parent 'Roberson Seedling' in most horticultural characteristics. However, 'Can Do Pink' differs in producing a shorter, more compact plant. Additionally, blooms of 'Can Do Pink' self clean spent petals faster and produce blooms that are a stable overall color, whereas the pollen parent produces blooms lacking stability in color.

COMMERCIAL COMPARISON

'Can Do Pink' can be compared to the unpatented commercial variety *Canna* 'Pink President.' Plants of 'Pink President' are similar to plants of 'Can Do Pink' in most horticultural characteristics, however, 'Can Do Pink' produces a shorter, more compact overall plant. Additionally, plants of 'Can Do Pink' produces flowers of true pink, rather than the salmon pink of 'Pink President.'

'Can Do Pink' can also be compared to the unpatented commercial variety *Canna* 'Liberty Watermelon.' Plants of 'Liberty Watermelon' are similar to plants of 'Can Do Pink' in most horticultural characteristics, however, 'Can Do Pink' produces a shorter, more compact overall plant. Additionally, plants of 'Can Do Pink' produces flowers of lighter pink than those of 'Liberty Watermelon.'

BRIEF DESCRIPTION OF THE PHOTOGRAPH

The accompanying photograph in FIG. 1 illustrates in full color a typical plant of 'Can Do Pink' grown outdoors in Lompoc, Calif. This plant is approximately 1 year old, shown in a 1 gallon pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Can Do Pink' plants grown in a greenhouse in Lompoc, Calif. Temperatures ranged from 10° C. to 20° C. at night to 12° C. to 25° C. during the day. No artificial light, photoperiodic treatments or chemical treatments were given to the plants. Measurements and numerical values represent averages of typical plant types.

Botanical classification: *Canna generalis*. cultivar 'Can Do Pink.'

Age of the plant described: Approximately 1 year.

Container size of the plant described: 1 gallon.

PROPAGATION

Time to initiate roots: About 5 days at temperatures of 25 to 28 degrees C.

Time to develop roots: About 21 days at temperatures of 28 to 31 degrees C.

Rhizome description: Near RHS White 155A in color covered with papery scale-like leaves near Brown 200B.

Root description: Thick, fibrous near RHS 158C in color.

PLANT

Growth habit: Upright.

Age of plant described: Approximately 1 year.

Container size: 1 gallon nursery container.

Height: Measured from top soil line of pot, approximately 28 cm to top of highest leaf. Approximately 49 cm to top of highest inflorescence.

Plant spread: Approximately 53 cm.

Growth rate: Rapid.

Branching characteristics: Non-branching, basal clump forming.

Stem:

*Length.*—Approximately 24 cm.
*Diameter.*—Approximately 1.9 cm.
*Texture.*—Glabrous, slightly ribbed.
*Color.*—Near RHS Yellow-Green 144A.

FOLIAGE

Leaf:

*Arrangement.*—Simple, alternate.
*Average length.*—Approximately 19 cm.
*Average width.*—Approximately 14 cm.
*Shape of blade.*—Ovate.
*Apex.*—Acute.
*Base.*—Symmetrical cuneate with sheathing.
*Margin.*—Entire.
*Texture of top surface.*—Smooth to slightly ridged, matte.
*Texture of bottom surface.*—Smooth, matte.
*Quantity of leaves per plant.*—Approximately 15.
*Color.*—Young foliage upper side: Near RHS Green 137A. Young foliage under side: Near RHS Green 137A. Mature foliage upper side: Near RHS Green 137A. Mature foliage under side: Near RHS Green 137A.
*Venation.*—Type: Pinnate. Venation color upper side: Near RHS Yellow-Green 144A. Venation color under side: Near RHS Yellow-Green 144A.

Petiole:

*Length.*—Average 7.2 cm.
*Diameter.*—Average 1 cm.
*Texture.*—Glabrous.
*Color.*—Near RHS Green 143C.

Sheath:

*Length.*—Approximately 5.5 cm.
*Width.*—Approximately 1 cm.
*Texture.*—Glabrous.
*Color.*—Near RHS Green 137B.

FLOWER

Natural flowering season: Spring and Summer.

Inflorescence description: Single flowers arranged on terminal racemes; several racemes per plant.

Flower longevity on plant: Individual flowers last approximately 2 weeks.

Quantity of flowers: Approximately 15 per raceme.

Inflorescence size:

*Height.*—Approximately 19 cm.
*Diameter.*—Approximately 15 cm.

Inflorescence sheath:

*Length.*—Approximately 9.5 cm.
*Diameter.*—Approximately 4.5 cm, unrolled, normally very tightly held to stem.
*Texture.*—Inner Surface: Finely ribbed. Outer surface. Finely ribbed.
*Color.*—Near RHS Yellow-Green 145C with stripes near Greyed-Purple 187A.

Peduncle:

*Length.*—Approximately 5.5 cm.
*Width.*—Approximately 1.0 cm.
*Color.*—Near RHS Yellow-Green 144B.
*Texture.*—Glabrous.
*Strength.*—Very strong.

Flowers:

*Flower form.*—Salverform.
*Flower diameter* (*at widest point*).—Approximately 10.5 cm.
*Flower length* (*height from the base of the pedicel*).—Approximately 9.5 cm.

Flower bud: (just before showing color)

*Length.*—Approximately 3.9 cm.
*Diameter.*—Approximately 0.9 cm.
*Shape.*—Narrow ovoid.
*Color.*—Near RHS Red 46C.

Bracts:

*Quantity.*—Average 3.
*Arrangement.*—Whorled.
*Length.*—Approximately 4.5 cm.
*Width.*—Approximately 1.9 cm.
*Shape.*—Elliptic.
*Apex.*—Acute.
*Base.*—Oblique.
*Margin.*—Entire.
*Texture.*—Glabrous.
*Appearance.*—Slightly shiny.
*Color.*—Inner Surface: Faint background coloration near RHS Yellow-Green 150D, at base, darkening to 137B and 137C near upper half. Prominent striping near Red-Purple 59B, margin near Red-Purple 59B. Outer surface: Faint background coloration near RHS Yellow-Green 150D, at base. Center coloration near Red 45A, top ⅓ of bract blade is Greyed-Purple 187B. Entire margin near Greyed-Purple 187B.

Pedicels:
*General description.*—Flattened, nearly fused to peduncle.
*Length.*—Approximately 0.5 cm.
*Diameter.*—Approximately 0.5 cm.
*Angle.*—About 45 degrees from Peduncle.
*Strength.*—Very strong.
*Texture.*—Succulent, glabrous.
*Color.*—Near RHS Green 143C.

Pedicel sheath:
*Texture.*—Chartaceous.
*Length.*—Approximately 2.0 cm.
*Width.*—Approximately 2.1 cm.
*Color.*—Near RHS Yellow-Green N144D background with striping near Greyed-Purple 187A.

Sepals:
*Quantity.*—Average 3.
*Appearance.*—Matte.
*Length.*—Approximately 1.1 cm.
*Width.*—Approximately 0.8 cm.
*Shape.*—Deltoid.
*Apex.*—Acute.
*Base.*—Cordate.
*Margin.*—Entire.
*Texture.*—Glabrous.
*Color.*—Inner Surface: Near RHS Yellow-Green 145B, Stripes and margin near Red-Purple 59C. Outer Surface: Near RHS Yellow-Green 145B, Stripes, apex and margin near Red-Purple 59C.

Petals:
*Quantity.*—4 actual petals; 2 petaloid staminoides described in separate section.
*Arrangement.*—Whorled.
*Length.*—Approximately 7.8 cm.
*Width.*—Approximately 4.9 cm.
*Shape* (*all petals*).—Spatulate.
*Apex* (*all petals*).—Obtuse, with irregular obtuse shallow lobes. Depth of lobes: approximately 0.3 cm.
*Base.*—Cuneate. Margin: Entire. Texture: Inner surface: Glabrous. Texture: Outer surface: Glabrous.
*Color.*—When opening, inner and outer surfaces: Near RHS Red-Purple 58B. Fully opened, inner surface: Near RHS Red 52A. Fully opened, outer surface: Near RHS Red 52A. Fading inner surface: Near RHS Red 54A. Fading outer surface: Near RHS Red 54A.

Primary/largest petaloid staminodia:
*Quantity.*—1.
*Length.*—Approximately 5.2 cm.
*Width.*—Approximately 0.9 cm.
*Shape.*—Narrow oblanceolate, asymmetrical, curling significantly to one side.
*Apex.*—Acute, curling.
*Base.*—Cuneate.
*Margin.*—Entire.
*Texture.*—All surfaces glabrous.
*Appearance.*—Shiny.
*Color.*—Upper (inner) surface: Near RHS Red 53D.
*Color.*—Lower (outer) surface: Near RHS Red 53D. Stamen Present on Primary Petaloid staminoidia.

Stamens:
*Number.*—1.
*Filament length.*—No filament.
*Anther length.*—Approximately 1.0 cm.
*Anther color.*—Near RHS Yellow-Orange 15D.
*Anther shape.*—Linear, undulating.
*Pollen.*—Moderate.
*Pollen color.*—Near RHS Yellow 13D.

Secondary petaloid staminode:
*Quantity.*—1.
*Length.*—Approximately 4.7 cm.
*Width.*—Approximately 0.8 cm.
*Shape.*—Linear.
*Apex.*—Acute.
*Base.*—Cuneate.
*Margin.*—Entire.
*Texture.*—Upper (inner) and lower (outer) surfaces: Glabrous.
*Appearance.*—Shiny.
*Color.*—Upper (inner) surface: Near RHS Yellow 11B, small blotches of Red 53A near apex and near base.
*Color.*—Lower (outer) surface: Near RHS Yellow 11B, small blotches of Red 53A near apex and near base.
*Fragrance.*—Very faint.

REPRODUCTIVE ORGANS

Stamens: See Primary petaloid staminode.

Gynoecium:

Pistil: Ovary present, no visible stigma or style.
*Ovary color.*—Near RHS Yellow-Green 145B.
*Ovary diameter.*—0.5 cm.
*Ovary height.*—0.7 cm.

OTHER CHARACTERISTICS

Seeds: Infrequent, low production of round, approximately 0.6 cm diameter seeds near RHS Brown 200B.

Disease/pest resistance: Neither resistance nor susceptibility to common diseases and pets of *Canna* have been observed in the new variety.

Temperature tolerance: Tolerates temperatures from approximately 4° C. to 38° C.

What is claimed is:

1. A new and distinct cultivar of *Canna generalis* plant named 'Can Do Pink' as herein illustrated and described.

* * * * *